(12) United States Patent
Zhang et al.

(10) Patent No.: US 11,058,616 B2
(45) Date of Patent: Jul. 13, 2021

(54) AEROSOL ANTIPERSPIRANT METHODS

(71) Applicant: The Procter & Gamble Company, Cincinnati, OH (US)

(72) Inventors: Jianwei Zhang, Mason, OH (US); Beverly Ann Herre, Liberty Township, OH (US); David Frederick Swaile, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 16/221,651

(22) Filed: Dec. 17, 2018

(65) Prior Publication Data
US 2019/0183747 A1    Jun. 20, 2019

Related U.S. Application Data

(60) Provisional application No. 62/599,850, filed on Dec. 18, 2017.

(51) Int. Cl.
| | | |
|---|---|---|
| *A61K 8/04* | (2006.01) | |
| *A61K 8/365* | (2006.01) | |
| *A61K 8/891* | (2006.01) | |
| *A61K 8/26* | (2006.01) | |
| *A61K 8/49* | (2006.01) | |
| *A61K 8/73* | (2006.01) | |
| *A61K 8/89* | (2006.01) | |
| *B65D 83/14* | (2006.01) | |
| *B65D 83/42* | (2006.01) | |
| *A61Q 15/00* | (2006.01) | |

(52) U.S. Cl.
CPC ........... *A61K 8/046* (2013.01); *A61K 8/26* (2013.01); *A61K 8/365* (2013.01); *A61K 8/4973* (2013.01); *A61K 8/732* (2013.01); *A61K 8/89* (2013.01); *A61K 8/891* (2013.01); *A61Q 15/00* (2013.01); *B65D 83/42* (2013.01); *B65D 83/752* (2013.01); *A61K 2800/31* (2013.01); *A61K 2800/48* (2013.01); *A61K 2800/56* (2013.01); *A61K 2800/5922* (2013.01); *A61K 2800/805* (2013.01); *A61K 2800/87* (2013.01)

(58) Field of Classification Search
CPC ........ A61K 8/046; A61K 8/365; A61K 8/891; A61K 8/26; A61K 8/4973; A61K 8/732; A61K 8/89; A61K 2800/48; A61K 2800/5922; A61K 2800/56; A61K 2800/31; A61K 2800/805; B65D 83/752; B65D 83/42; A61Q 15/00
See application file for complete search history.

(56) References Cited

U.S. PATENT DOCUMENTS

| | | |
|---|---|---|
| 2,852,404 A | 9/1958 | Satterthwaite |
| 3,887,692 A | 6/1975 | Gilman |
| 3,904,741 A | 9/1975 | Jones et al. |
| 4,152,416 A | 5/1979 | Spitzer et al. |
| 4,359,456 A | 11/1982 | Gosling et al. |
| 4,396,152 A | 8/1983 | Abplanalp |

(Continued)

FOREIGN PATENT DOCUMENTS

| | | |
|---|---|---|
| EP | 1417953 A2 | 5/2004 |
| WO | 199604884 A1 | 2/1996 |
| WO | 2003002082 A1 | 1/2003 |

*Primary Examiner* — Trevor Love
(74) *Attorney, Agent, or Firm* — Kathleen Y. Carter

(57) ABSTRACT

An aerosol antiperspirant product method of manufacture is provided, in which the time between the final milling of an antiperspirant composition and its filling into a spray device is at most 2 hours.

14 Claims, 6 Drawing Sheets

(56) References Cited

U.S. PATENT DOCUMENTS

| | | | |
|---|---|---|---|
| 4,411,883 | A | 10/1983 | Kenkare et al. |
| 4,806,338 | A | 2/1989 | Smith |
| 4,840,786 | A | 6/1989 | Johnson et al. |
| 4,871,525 | A | 10/1989 | Giovanniello et al. |
| 4,904,463 | A | 2/1990 | Johnson et al. |
| 4,935,224 | A | 6/1990 | Russo et al. |
| 5,298,236 | A | 3/1994 | Orr et al. |
| 5,605,682 | A | 2/1997 | Ross et al. |
| 5,672,699 | A | 9/1997 | Billmers et al. |
| 5,711,941 | A | 1/1998 | Behan et al. |
| 5,776,476 | A | 7/1998 | Billmers et al. |
| 5,814,309 | A | 9/1998 | Panitch |
| 5,861,144 | A | 1/1999 | Peterson et al. |
| 6,037,466 | A | 3/2000 | Maliczyszyn et al. |
| 7,375,214 | B2 | 5/2008 | Lewis |
| 7,799,909 | B2 | 9/2010 | Lewis |
| 7,815,899 | B2 | 10/2010 | Smith |
| 8,147,808 | B2 | 4/2012 | Scavone et al. |
| 8,518,425 | B2 | 8/2013 | Chan et al. |
| 9,186,642 | B2 | 11/2015 | Dihora et al. |
| 9,905,531 | B2 | 2/2018 | Radu et al. |
| 9,993,793 | B2 | 6/2018 | Dihora et al. |
| 2006/0104918 | A1 | 5/2006 | Brown et al. |
| 2007/0292460 | A1 | 12/2007 | Schiemann et al. |
| 2010/0104613 | A1 | 4/2010 | Unilever |
| 2011/0269657 | A1 | 11/2011 | Dihora et al. |
| 2014/0077003 | A1 | 3/2014 | Swaile |
| 2015/0023887 | A1 | 1/2015 | Swaile et al. |
| 2015/0283046 | A1 | 10/2015 | Swaile et al. |
| 2017/0290751 | A1 | 10/2017 | Doering |

| Mixing Time, hr | Sample 1 viscosity, cP |
|---|---|
| 0.00 | 3825 |
| 0.20 | 2520 |
| 0.50 | 2060 |
| 1.00 | 1780 |
| 2.00 | 1420 |
| 4.00 | 1380 |
| 6.00 | 1330 |
| 10.00 | 1480 |

US 11,058,616 B2

AEROSOL ANTIPERSPIRANT METHODS

CROSS REFERENCE TO RELATED APPLICATION

This application claims the benefit of U.S. Provisional Application No. 62/599,850, filed Dec. 18, 2017, the substance of which is incorporated herein by reference.

TECHNICAL FIELD

One aspect of the invention relates generally to methods of manufacture of antiperspirant compositions and products, including spray devices containing an antiperspirant composition and a propellant.

BACKGROUND

Body odor may be generated in the area under the arms due to a high concentration of sweat glands. While perspiration is odorless, it contains natural oils that can be nutrient source for bacteria living on the skin. These bacteria interact with the natural oils, converting them into odor producing compounds. Antiperspirant compositions contain an active, such as an aluminum salt, that reacts with the electrolytes in perspiration to form a plug in the ducts of sweat glands. The plugs prevent perspiration from exiting the duct, thereby depriving the bacteria of water and a food source. Antiperspirant compositions may be applied to the skin in either a contact type product form, e.g., a stick or roll-on, or non-contact type product form, such as an aerosol spray. Aerosol spray devices that dispense an antiperspirant composition are known in the art. Various examples are described in U.S. Pat. Nos. 4,152,416; 4,806,338; 4,840,786; 4,904,463; 4,935,224; 5,298,236; 5,605,682; 5,814,309; 7,815,899; EP 674,899; WO 96/04884; WO 2004/014330; and WO 2007/001842.

While users of aerosol sprays are accustomed to shaking a spray device before use, the general user expectation is that a spray device produces a spray that comes out easily and evenly. Having to excessively or vigorously shake the spray device before use or using a spray device that becomes clogged or difficult to spray are undesirable consumer experiences. Therefore, there is a continuing need for compositions and products that can be filled into a spray device and easily released without any choking or clogging of the spray device.

SUMMARY OF THE DISCLOSURE

In accordance with one aspect, a method of making an aerosol antiperspirant product, the method comprising:
  combining components to form a composition, said components selected from the group consisting of an antiperspirant active, a carrier, a suspending agent, clay activator, and combinations thereof;
  milling the composition;
  depositing the composition into a spray device at most about 2 hours after milling the composition; and
    adding a propellant to the composition in the spray device;
  wherein the composition does not include cyclopentasiloxane.

BRIEF DESCRIPTION OF THE DRAWINGS

While the specification concludes with claims, it is believed that the same will be better understood from the following description taken in conjunction with the accompanying drawings wherein like numbers illustrate like elements throughout the views and in which:

DETAILED DESCRIPTION

Figure 1:
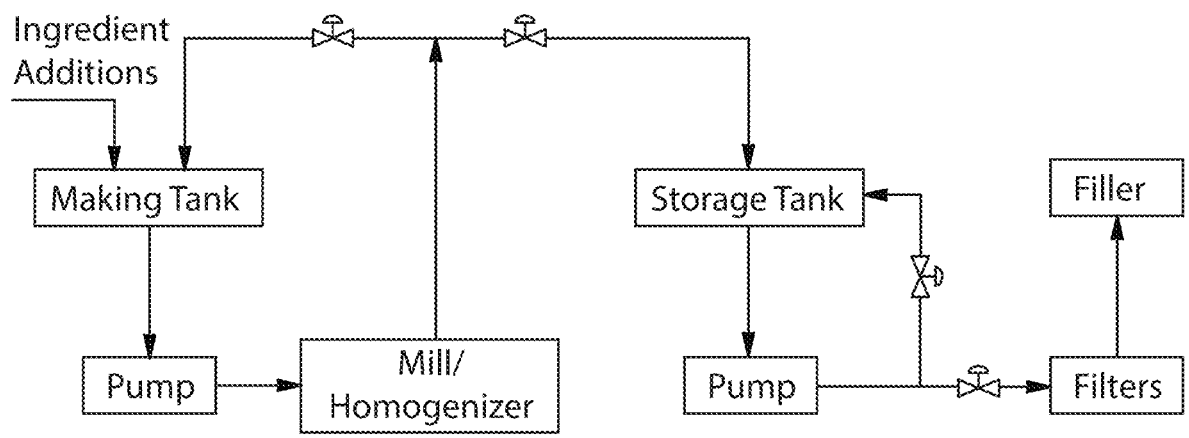
FIG. 1 is a flowchart showing a method of manufacturing of aerosol compositions and products.

A spray device, container, composition, propellant, etc. may comprise, consist essentially of, or consist of, various combinations of the materials, features, structures, and/or characteristics described herein.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the antiperspirant composition (or formulation), unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. The term "molecular weight" or "M.Wt." as used herein refers to the number average molecular weight unless otherwise stated.

The term "antiperspirant composition" refers to any composition containing an antiperspirant active and which is intended to be sprayed onto skin, exclusive of a propellant.

The term "antiperspirant efficacy" refers to the amount of wetness protection provided by application of an antiperspirant composition to an underarm area (or axillia) by a spray device. Antiperspirant efficacy may be quantified by the amount (mg) of sweat collected following exposure to a hot room compared to a baseline amount.

The term "bulking or suspending material" refers to a material which is intended to reduce settling of a particulate from a liquid and/or reduce the severity of particulate caking post settling.

The term "deposition efficiency" refers to the percentage of a material (e.g., antiperspirant active, fragrance material, antiperspirant composition, etc.) that is deposited on a target surface compared to the amount of material that exits a spray device.

The term "particulate" refers to a material that is solid or hollow or porous (or a combination thereof) and which is substantially or completely insoluble in the liquid materials of an antiperspirant composition.

The term "propellant" refers to one or more gases that are used to pressurize the antiperspirant composition to facilitate egress of the antiperspirant composition from the container. Some propellants may be a mixture of gases (e.g., A-46 which may be a mixture of isobutane, butane and propane). A propellant may be in the form of a liquid (i.e., a liquefied gas) when under pressure within the reservoir of a spray device. In addition, a propellant may be in its gaseous state within the head space of the reservoir. A propellant may be present in both a liquefied form and its gaseous state within the reservoir. Unless specified otherwise (e.g., liquid propellant or gaseous propellant), the term propellant is intended to encompass the liquefied form and the gaseous state individually and collectively.

The term "substantially free of" refers to an amount of a material that is less than 1%, 0.5%, 0.25%, 0.1%, 0.05%, 0.01%, or 0.001% by weight of an antiperspirant composition. "Free of" refers to no detectable amount of the stated material, ingredient or thing.

The term "total fill" refers to the total amount of materials added to or stored within a reservoir(s) of a container. For example, total fill includes the propellant and antiperspirant composition stored within a spray device after completion of filling and prior to first use.

The term "viscosity" means dynamic viscosity (measured in centipoise, cPs, or Pascal-second, Pa·s) or kinematic viscosity (measured in centistokes, cSt, or m$^2$/s) of a liquid at approximately 25° C. and ambient conditions. Dynamic viscosity may be measured using a rotational viscometer, such as a Brookfield Dial Reading Viscometer Model 1-2 RVT available from Brookfield Engineering Laboratories (USA) or other substitutable model as known in the art. Typical Brookfield spindles which may be used include, without limitation, RV-7 at a spindle speed of 20 rpm, recognizing that the exact spindle may be selected as needed by one skilled in the art. Kinematic viscosity may be determined by dividing dynamic viscosity by the density of the liquid (at 25° C. and ambient conditions), as known in the art.

Method of Manufacture

Many current antiperspirant aerosol products use suspending or bulking agents, such as clay-based materials, to help build the product structure. These clay-based materials are combined with other components, such as carriers, antiperspirant actives, skin feel modifiers, clay activators, masking agents, perfumes, and other materials, into an antiperspirant composition, which is then milled to delaminate the clay. This milling process (a machining process using rotary cutters) raises the viscosity of the antiperspirant composition. After milling, the antiperspirant composition is typically transferred to a storage tank where it undergoes continuous mixing to prevent product separation and to ensure batch homogeneity. The antiperspirant composition is then filled into individual spray devices and propellant is added to the composition in the spray device, thus forming an aerosol antiperspirant product. The consumer typically shakes the spray device before use, which is sufficient for the aerosol product to not choke or clog the spray device, or otherwise distract from the consumer spray-on experience.

However, in some instances, differences in the formulations of the compositions may result in variance of the product's structure such that it becomes damaged by the process described above. The present inventors have observed that in some cases, such as a formulation change to a liquid carrier that does not as easily wet the clay, the viscosity of the antiperspirant composition may decrease quickly under normal mixing conditions in the storage tank. For example, antiperspirant compositions that do not include cyclopentasiloxane may experience this. This less structured and lower viscosity composition tends to sediment faster and form compacted cake. As the low-viscosity composition is filled into a spray device and propellant is added, the resulting aerosol antiperspirant product may require higher energy to redisperse the product in order for it to function as intended. In other words, the lower viscosity composition may result in an aerosol product that requires shaking beyond what a typical consumer will provide, and thus the spray device may clog and diminish the consumer experience.

The present inventors have discovered that adding a milling step immediately before filling the antiperspirant composition into the spray devices raises the viscosity and provides more structure to the composition, which results in an aerosol product that does not clog the actuator of the spray device. This more structured and higher viscosity antiperspirant composition also results in lower settling velocity after shaking, more uniform sprays, and improves other viscosity-related product behaviors, such as product deposition, that can lead to more consumer benefits. Addition of a milling step within 2 hours of filling the composition into individual spray devices allows for the filling to occur before any separation of the composition and also negates the need for mixing before the filling.

Figure 2:
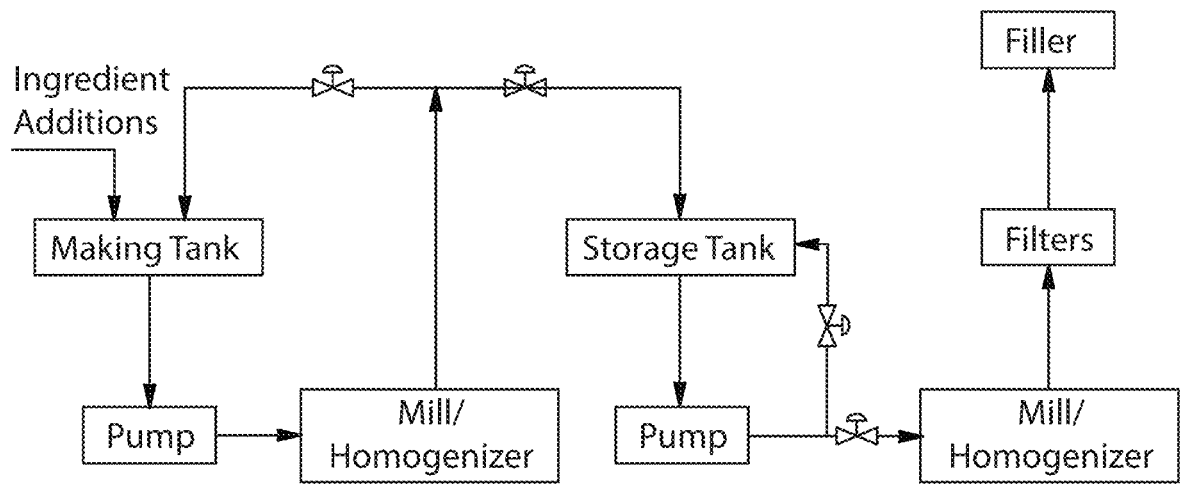
FIG. 2 is a flowchart showing a method of manufacturing of aerosol compositions and products of the present invention.
Figure 3:
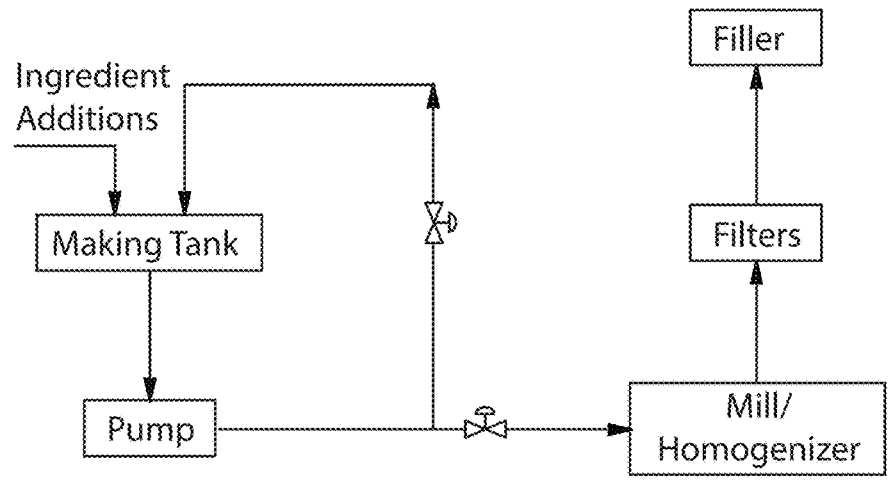
FIG. 3 is a flowchart showing a method of manufacturing of aerosol compositions and products of the present invention.

As shown in FIGS. 1-3, the present invention may include the step of milling the antiperspirant composition within 2 hours of the composition being filled into individual spray devices.

To begin the typical manufacturing process, the antiperspirant composition components may be combined in a large making tank. These components may comprise one or more materials selected from the group consisting of bulking or suspending agents, such as clay-based materials; clay activators; antiperspirant actives; carriers; skin feel modifiers; perfumes and fragrances; masking agents; starches; and combinations thereof. These composition components are then pumped over to be milled. At this point after the milling, the antiperspirant composition has a high viscosity, defined as at least about 2000 cP. The composition may be pumped to a large storage tank, where a low shear mixer may mix the composition. In some cases, the composition may sit in the storage tank while portions are pulled away to be filled in spray devices.

FIG. 1 depicts a process. Ingredients (antiperspirant composition components) may be added to a making tank, and then pumped to a mill/homogenizer. In some embodiments, this ingredient addition can be done first by combining the carrier solvent and clay and milling them. This material may be cycled back to the making tank, where the clay activator may be added, with the total composition milled again. Finally, the material may be cycled back to the making tank again, and all the powder materials may be mixed in and then milled. The component additions may be performed by a powder disperser (like Quadro) or by adding to the tank directly. The antiperspirant composition may be mixed to a homogeneous state. In various places along the process path there may be valves to direct the flow, that by closing or opening certain valves, the content in the container can be directed back for recirculation or continuous milling, or for flow on to the storage tank. Also, some components may be added after milling if they cannot withstand the milling.

In some cases, such as the process depicted in FIG. 1, portions of the antiperspirant composition may be removed from the large storage tank, sent through filters and then to a filler that will fill individual spray devices. Filling spray devices this way may take several days, resulting in a portion of the composition remaining in the storage tank for some time with only a low shear mixer. When there is no additional milling step after the antiperspirant composition is in the storage tank, the antiperspirant composition will typically wait at least 6 or 8 hours after being milled before a first portion is sent to be filled into a spray device. For much of the antiperspirant composition in the storage tank, it will be longer, even up to several days, between the final milling and being filled into a spray device. Some formulations of the composition may maintain viscosity during this time, but the present inventors have discovered that other formulations, particularly formulations without certain volatile liquids (e.g., cyclopentasiloxane and other similar liquids) as a carrier, lose viscosity over time in the storage tank. It is believed that the lower viscosity antiperspirant composition, if sent to the filler to be put into a spray device, is compacted to a degree such that more energy, i.e. shaking, is required to fully redisperse or homogenize the material.

As such, the present inventors have discovered that a milling step immediately before the antiperspirant composition is sent to the filler raises the viscosity sufficiently that once the composition is filled into a spray device and propellant is added, the spray device does not choke or clog. This inventive process is depicted in FIG. 2. By immediately, it is meant that the antiperspirant composition is filled into a spray device at most about 5 hours after the final milling step. In some cases, the antiperspirant composition may be filled into a spray device at most about 4 hours, at most about 3 hours, at most about 2 hours, at most about 90 minutes, at most about 60 minutes, at most about 45 minutes, at most about 30 minutes, at most about 20 minutes, or at most about 10 minutes after the final milling step. Many embodiments herein describe at most 2 hours between milling and filling, but in each embodiment, the time between milling and filling may be any of the times described above, including at most 5 hours. The viscosity of the antiperspirant composition when filled into the spray device may be at least about 1500 cP, at least about 2000 cP, at least about 2500 cP, at least about 3000 cP, and in some instances, at least about 4000 cP.

In FIG. 2, the mixing of the antiperspirant composition components is similar to that as described for FIG. 1. After all components of the antiperspirant composition have been added and milled, the antiperspirant composition may be moved to a storage tank, where it may wait anywhere from several hours to several days. In FIG. 2, the antiperspirant composition, or a portion of the antiperspirant composition, may be moved from the storage tank and milled a final time. After this final milling, the antiperspirant composition, with its bolstered viscosity, may be sent to the filler to be filled into spray devices after no more than about 2 hours, and in some embodiments, within 30 minutes of the final milling. Said another way, the time between the antiperspirant composition's final milling and when it is filled into a spray device may be less than 2 hours.

There are numerous ways that the process may be conducted while still having the final milling occur at most about 2 hours or at most about 5 hours before filling the antiperspirant composition into spray devices. In some embodiments, such as that depicted in FIG. 3, rather than combining all the components of the antiperspirant composition, milling them, and then mixing them in a large storage tank awaiting a second milling immediately before filling, the antiperspirant composition components may be combined in a smaller quantity, such that a large storage tank is not necessary. The combined components for the antiperspirant composition may be milled a single time, sent through filters, and then filled into spray devices with at most about 2 hours between the milling and filling. In some embodiments, the time between milling and filling may be at most about 5 hours. In addition, during these 2 or 5 hours, the antiperspirant composition may be at rest, that is, there is no mixing necessary before filling the composition into a spray device. Thus, such a process is a semi-continuous process and does not require large making or storage tanks, or the low shear mixer, or the second milling. But it still allows high viscosity antiperspirant composition to be sent to the filler to be placed in spray devices. In some of these embodiments, the antiperspirant composition is filled into a spray device at most about 2 hours after the final milling step, as described above. In FIG. 3, the mixing of the antiperspirant composition components is similar to that as described for FIG. 1. After all components of the antiperspirant composition have been added and milled, the antiperspirant composition may be sent to the filler to be filled into spray devices after no more than about 2 hours, and in some embodiments, within 30 minutes of the final milling. In this process, there is no need for an additional milling step, but rather the entire process is done in a semi-continuous way.

In some embodiments, after the single or final milling, but within the 2 hours before the composition is deposited into a spray device, the composition may be sent through a Cuno filter and/or an additional screen filter before being sent to the filler. Also, it is noted that the processes herein, even the semi-continuous process done in smaller quantities, are contemplated to be for commercial quantities, wherein the batches of antiperspirant composition in the making tank and/or storage tanks are at least about 500 kilograms, in some cases at least about 1000 kilograms.

More specifically, FIGS. 2 and 3 show possible inventive processes, each of which include the step of a final milling of the antiperspirant composition at most 2 hours (in some embodiments up to about 5 hours, and in some embodiments as little as 10 minutes) before filling the antiperspirant composition into a spray device.

Aerosol Composition

I. Propellants

A spray device comprises a propellant stored in one or more reservoirs of the container. The propellant may be stored in the same reservoir as an antiperspirant composition or a separate reservoir, although it is preferred that the propellant is stored within the same reservoir as the antiperspirant composition. The propellant may be present in a liquefied form that is miscible with liquid carriers of the antiperspirant composition as well as gaseous state within a head space of the reservoir. The liquid propellant and the antiperspirant composition form a mixture that travels through the container, eventually exiting the container where the liquid propellant vaporizes to from a spray. The propellant may have a concentration from about 60% to about 90% or 95% or from about about 70% to about 80% or from about 80% to about 90%, by weight of the antiperspirant product. Generally, as propellant concentration increases through these higher concentrations, the discharge may tend be more "gassy" possibly resulting in less deposition of the antiperspirant composition on the target surface as well as a wider spray pattern.

A wide variety of propellants may be used with the spray devices and antiperspirant compositions described herein, although in some embodiments the spray device is substantially free of compressed gas propellants such as nitrogen, air and carbon dioxide. Some suitable propellants may have a boiling point (at atmospheric pressure) within the range of from about −45° C. to about 5° C. Some suitable propellants may include chemically-inert hydrocarbons such as propane, n-butane, isobutane and cyclopropane, and mixtures thereof, as well as halogenated hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Some propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), HFO1234 (trans-1,3,3,3-tetrafluoropropene) and 152A (1,1 difluoroethane).

II. Antiperspirant Compositions

A. Antiperspirant Composition Viscosity

In some embodiments, it may be desirable for the viscosity of the antiperspirant composition to be from about 2,000 centipoise, 3,000 centipoise, 4,000 centipoise, 5000 centipoise, or 7,000 centipoise to about 50,000 centipoise 40,000 centipoise, or 30,000 centipoise, or 20,000 centipoise, or 10,000 centipoise, or 7,000 centipoise, 5,000 centipoise or 4,000 centipoise at 25° C. (1 centipoise being equal to $1 \times 10^{-3}$ Pa·s). It is believed that a viscosity lower than 1,000 centipoise may lead to an antiperspirant composition, which when spayed, results in a runny or drippy effect on skin. This may be perceived by a user as having a wet rather than dry feel. For comparison, roll-on type antiperspirant compositions often have viscosities below 1,000 centipoise, because the roll-on applicator utilizes a roller ball to apply a thin film of the antiperspirant composition thereby minimizing a runny or drippy effect.

An antiperspirant composition should be flowable so that it may be sprayed effectively from a spray device. Therefore in certain aspects, the aerosol antiperspirant composition may be devoid of sufficient concentrations and/or substantially free of ingredients that provide thickened stick or gel type of rheology in antiperspirant stick or gel products. Some common agents which may be excluded in sufficient amounts include hydrogenated castor oil, solid paraffins, silicone waxes, and mixtures thereof.

B. Non-Volatile Silicone Fluids

The antiperspirant compositions may comprise one or more non-volatile silicone fluids. The non-volatile silicone fluid may function as the primary or principal liquid carrier for the antiperspirant active. As used herein, the term "non-volatile" refers to a material that has a boiling point above 250° C. (at atmospheric pressure) and/or a vapor pressure below 0.1 mm Hg at 25° C. Conversely, the term "volatile" refers to a material that has a boiling point less than 250° C. (at atmospheric pressure) and/or a vapor pressure about 0.1 mm Hg at 25° C. Incorporating a non-volatile silicone fluid in an antiperspirant composition may provide several benefits. First, non volatile silicone fluids can be more effectively deposited on the skin than volatile silicone fluids from aerosol antiperspirant compositions containing high levels of propellant, such as greater than 60% or 80% propellant. Deposition of high concentrations of a non-volatile carrier fluid in the antiperspirant composition is believed to reduce visible white residue at application, reduce visible white residue throughout the day and reduce antiperspirant composition transfer to clothes while dressing. Second, incorporating a non-volatile silicone fluid may increase the substantivity of the antiperspirant composition on skin, thereby potentially increasing antiperspirant efficacy, as the antiperspirant composition may form a film that more readily adheres to skin rather than flaking off or transferring to clothing throughout the day. Third, incorporating a non-volatile silicone fluid may also decrease the propensity for a visible residue to appear on skin (compared to using a volatile silicone fluid), as the non-volatile silicone fluid does not evaporate thereby leaving behind the white antiperspirant active as a visible residue. However, incorporating a non-volatile silicone fluid is not without potential tradeoffs. A perception of wetness post application (which may be undesirable for some consumers) is one tradeoff that may be associated with high concentrations of a non-volatile silicone fluid in an antiperspirant composition.

The total concentration of non-volatile, silicone fluids may be from about 30%, 35%, 40%, 45%, 50% to about 70%, 65%, 60%, 55% or 50% by weight of an antiperspirant composition. In some embodiments, the total concentration of non-volatile, silicone fluids may be from about 35% or 45% to about 55% by weight of an antiperspirant composition. The liquid materials of the antiperspirant composition may consist essentially of or primarily comprise a non-volatile, silicone fluid(s). Some non-volatile, silicone fluids that may be used include, but are not limited to, polyalkyl siloxanes, polyalkylaryl siloxanes, and polyether siloxane copolymers, and mixtures thereof. Some preferred non-volatile silicone fluids may be linear polyalkyl siloxanes, especially polydimethyl siloxanes (e.g., dimethicone). These siloxanes are available, for example, from Momentive Performance Materials, Inc. (Ohio, USA) under the tradename Element 14 PDMS (viscosity oil). Silicones Fluids from Dow Corning Corporation (Midland, Mich., USA) available under the trade name Dow Corning 200 Fluid series (e.g., 3 to 350 centistokes). Other non-volatile silicone fluids that can be used include polymethylphenylsiloxanes. These siloxanes are available, for example, from the General Electric Company as SF 1075 methyl phenyl fluid or from Dow Corning as 556 Fluid. A polyether siloxane copolymer that may be used is, for example, a dimethyl polyoxyalkylene ether copolymer fluid. Such copolymers are available, for example, from the General Electric Company as SF-1066 organosilicone surfactant. The non-volatile, silicone fluid may have an average viscosity from about 3 centistokes, 5 centistokes, 10 centistokes, 20 centistokes, or 50 centistokes to about 350 centistokes, 200 centistokes, 100 centistokes, 50 or 30 centistokes at 25° C. (1 centistoke being equal to $1 \times 10^{-6}$ m$^2$/s). In some specific embodiments, the silicone fluid may have a viscosity from about 5 centistokes to about 100 centistokes or 5 centistokes to about 50 centistokes or about 5 centistokes to about 30 centistokes.

Higher viscosity non-volatile silicone fluids (e.g., greater than 100 centistokes or 200 centistokes or 350 centistokes) are preferably mixed with lower viscosity, non-volatile silicone fluids to achieve an appropriate antiperspirant composition viscosity in combination with the concentration of particulates. High viscosity, non-volatile silicone fluids (e.g., greater than 100, 200, or 350 centistokes) may comprise less than 25% by weight of an antiperspirant composition.

In some instances, the non-volatile silicone fluid is a polydimethylsiloxane fluid (also commonly referred to as dimethicone). It will be appreciated that a polydimethylsiloxane fluid may be further characterized by, optionally, its viscosity or its molecular weight or its formula or a combination thereof. In some instances, the polydimethylsiloxane fluid may have the following characteristics:

TABLE 1

| Viscosity | Approximate Molecular Weight[1] | Approximate Average Number of Monomer Units in the Polymer[1] |
| --- | --- | --- |
| 5 Centistokes | 800 | 9 |
| 10 Centistokes | 1200 | 13 |
| 20 Centistokes | 2000 | 27 |
| 30 Centistokes | 2600 | 35 |
| 50 Centistokes | 3800 | 50 |
| 100 Centistokes | 6000 | 80 |
| 200 Centistokes | 9400 | 125 |
| 350 Centistokes | 13,700 | 185 |

[1]The compositions of Examples herein, to the extent they contained a dimethicone fluid, were formulated utilitizing a Dow Corning DC200 series fluid, which is believed to have had average molecule weights and average number of monomer subunits falling within the approximate values of Table 1.

The polydimethylsiloxane fluid may have the following formula (II):

$$M\text{-}D_X\text{-}M$$

wherein M is $(CH_3)_3SiO$ and D is $2CH_3(SiO)$ and X is equal to the average number of monomer units (see, e.g., Table 1) in the polymer minus 2. In some embodiments, X may be from about 6 to about 185, from about 9 to about 125, from about 9 to about 80, from about 9 to about 50, from about 13 to about 50 or from about 27 to about 50. In other embodiments, X may be from about 6 to about 35, from about 9 to about 35 or from about 13 to about 35. The term "approximate" as used in Table 1 refers to ±10% of a given value.

While a wide variety of non-volatile silicone fluids or oils may be used in an antiperspirant composition, in some instances it may be desirable for the non-volatile silicone fluid(s) to consist essentially of or consist of or consist primarily of non-functionalized silicone fluids. In some embodiments, it may be further desirable for the non-volatile silicone fluid(s) to be substantially or completely free of non-functionalized siloxanes capable of reacting with the antiperspirant active via an acid-base reaction or a chelation reaction. This is in contrast to, for instance, U.S. Pat. No. 4,806,338 which proposes the use of functionalized siloxanes. Functionalized siloxanes may in some instances be disadvantageous in that they may react with the antiperspirant active, either via an acid-base reaction in the case of aminofunctional silicones, which are Lewis bases (the antiperspirant actives are Lewis acids), or via a chelation reaction (in the case of the carboxy functional silicones), which reactions can reduce the efficacy of the antiperspirant active. In addition, functional silicones of the type taught by U.S. Pat. No. 4,806,338 may have reduced solubility in the propellant (and vice versa) which may give rise to inhomogeneity in the product with resultant inhomogeneity of deposition on skin.

C. Solvent

An aerosol composition may comprise a solvent. The solvent can be volatile, non-volatile, or a combination thereof. The composition can include from about 10% to about 80%, by weight of the composition, of solvent. In addition, the composition can comprise from about 10%, from about 15%, from about 20%, to about 50%, to about 60%, to about 70%, to about 80%, or any combination thereof, by weight of the composition, of solvent.

Volatile Solvents

The compositions described herein may include a volatile solvent or a mixture of volatile solvents. The volatile solvents may comprise from about 2%, from about 5%, from about 8%, from about 10%, from about 15%, from about 20%, to about 20%, to about 25%, to about 30%, to about 35%, to about 40%, to about 50%, about 60%, about 70%, about 80%, or any combination thereof, by weight of the composition, of volatile solvent. The volatile solvents useful herein may be relatively odorless and safe for use on human skin. Suitable volatile solvents may include $C_1$-$C_4$ alcohols and mixtures thereof. For example, ethanol may be used as the volatile solvent. Some other non-limiting examples of volatile solvents include methanol, propanol, isopropanol, butanol, and mixtures thereof.

Nonvolatile Solvents

The composition may comprise from about 2%, from about 5%, from about 8%, from about 10%, from about 15%, from about 20%, to about 20%, to about 25%, to about 30%, to about 35%, to about 40%, to about 50%, to about 60%, to about 70%, to about 80%, or any combination thereof, by weight of the composition, of nonvolatile solvent. The composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof. The composition may also be free of nonvolatile solvents.

B. Liquid Fragrance Materials

An antiperspirant composition may also optionally comprise one or more liquid fragrance materials. Liquid fragrance materials are typically a mixture of perfume or aromatic components that are optionally mixed with a suitable solvent, diluent or carrier. Some suitable solvents, diluents or carriers for the perfume components may include ethanol, isopropanol, diethylene glycol monoethyl ether, dipropylene glycol, diethyl phthalate, triethyl citrate, isopropyl myristate and mixtures thereof. An antiperspirant composition may comprise from about 0.5%, 0.75%, 1%, 2%, 3% or 4% to about 10%, 8%, 6%, or 4%, 3% or 2% by weight of a liquid fragrance material.

The perfume component may be any natural or synthetic perfume component known to one skilled in the art of creating fragrances including, but not limited to, essential oils, citrus oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Some non-limiting examples of perfume components include: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenyl-carbinyl acetate, p-tert.butyl-cyclohexyl acetate, isononyl acetate, vetiveryl acetate, vetiverol, alpha-n-amylcinammic aidehyde, alpha-hexylcinammic aldehyde, 2-methyl-3-(p-tert.butylphenyl)-propanol, 2-methyl-3-(p-isopropylphenyl)-propanal, 3-(p-tert.butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyltetrahydropyran, methyldihydrojasmonate, 2-n-heptylcyclopentanone, 3-methyl-2-pentylcyclopentanone, n-decanal, 9-decenol-1, phenoxyethyl isobutyrate, phenyl-acetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylionones, irones, cis-3-hexenol and esters thereof, indane musk fragrances, tetralin musk fragrances, isochroman musk fragrances, macrocyclic ketones, macrolactone musk fragrances, ethylene brassylate, aromatic nitro-musk fragrances. Some perfume components are also described in Arctander, Perfume and Flavour Chemicals (Chemicals), Vol. I and II (1969) and Arctander, Perfume and Flavour Materials of Natural Origin (1960).

C. Other Liquid Materials

It is contemplated that other liquid materials may be optionally included in an antiperspirant composition. The liquid materials of the antiperspirant composition may comprise less than 30%, 20%, 10%, or less than 5% by weight of liquid materials other than non-volatile, silicone fluids. Said in another way, the liquid materials of the antiperspirant composition may comprise more than 70%, 75%, 80%, 85%, 90% or about 100% by weight of non-volatile silicone fluids.

An antiperspirant composition may comprise less than 10%, 5%, 1%, or 0.5% by weight of a volatile silicone fluid. An antiperspirant composition may be substantially or completely free of a volatile silicone fluid.

An antiperspirant composition may optionally comprise one or more silicone gums. The term "gum" is used to refer to a material that has a viscosity within the range from about 100,000 to about 100 million centistokes at 25° C. and which is slowly flowable, as opposed to a rigid solid, which is not flowable, or a liquid, which is too flowable. Silicone gum materials are blends of a silicone gum and a diluents, wherein the diluents reduces the viscosity of the blend. Some common diluents can include but are not limited to 5 centistoke dimethicone, 50 centistoke dimethicone, 100 centistoke dimethicone or cyclopentasiloxane. In some embodiments, the antiperspirant composition may be substantially or completely free of cyclopentasiloxane. The silicone gum may comprise high viscosity polydimethylsiloxanes with terminal methyl (e.g., dimethicone) or hydroxyl (e.g., dimethiconol) groups. Silicone gums may have a molecular weight from 100,000 Daltons greater than 2,000,000 Daltons. The viscosity of the silicone gums (without a diluents) may range from 300,000 centistokes to greater than 2,500,000 centistokes or higher compared to the viscosity of silicone gum materials (inclusive of diluents) which may be less than 10,000 centistokes. Some examples of silicone gums and silicone gums materials include, but are not limited to, quaternary ammonium functional silicones such as DC7-6030 available from Dow Corning and 34720, 34749, 34731, 33134, SF-96, SF-1066, SF18 (350), SE30 and SE32 available from General Electric.

A silicone gum (or silicone gum material) may be added to an antiperspirant composition to further increase deposition and/or substantivity of the antiperspirant composition and/or increase the drop size of the aerosol spray particles. The improvement in deposition can be illustrated by evaluating the deposition of a test sample comprising 85% A46 propellant, 14.64% 50 centistoke dimethicone, and 0.36% DC1503 (note this is made by mixing 97% 50 cst dimethicone with 3% DC1503, which contains 12% silicone gum, and then adding that mixture to the propellant at a 15%). Deposition testing of this sample using the same valve and accuator as the aforementioned samples showed a deposition efficiency of about 58%. This represents a 38% improvement in deposition versus the aforementioned test sample comprising only 50 cst dimethicone and a more than 100% improvement over the sample comprising only cyclopentasiloxane. Maximizing liquid deposition in the test sample comprising a high concentration of a non-volatile silicone fluid and a high propellant concentration is desirable not only to reduce visible white but also to reduce potential inhalation hazards. Volatile silicones, such as cyclopentasiloxane, may be removed from the lung via exhaling while nonvolatile materials are less likely to be removed by the mechanism. As such it is desirable to limit inhalable non-volatile silicone materials by increasing the deposition efficiency via the addition of silicone gum.

However, formulating an antiperspirant composition with a silicone gum in combination with relatively high concentrations of a non-volatile silicone fluid and/or relatively high concentrations of total particulates may involve a number of tradeoffs. For example, too much of a silicone gum may dramatically increase viscosity of the antiperspirant composition and the risk of clogging of the container actuator and/or valve, particularly where there is already a relatively high concentration of total particulates. Still further, too much of a silicone gum may reduce the diameter of the spray making it more difficult for a user to achieve complete coverage of an axillia (typically a 7.5 cm×12.5 cm area) during application as well as potentially creating regions of high antiperspirant composition dosage, thereby potentially impacting skin feel. Further, some silicone gums, such as the quarternary ammonium functional silicones described in U.S. Pat. No. 7,815,899 may have an undesirable odor (e.g., a fish-like odor) associated therewith, which may then be imparted to an antiperspirant composition in some instances.

Generally, it is believed that the concentration of the silicone gum may be increased as propellant concentration increases, all other variables being equal. Conversely, it is believed that as the amount of particulates increases, the concentration of the silicone gum should be decreased as the amount of particulates increases, all other variables being equal. This is believed particularly true within the particulate range of 40% to 60% by weight of the antiperspirant composition, as mounding of the antiperspirant composition may result.

Given the one or more potential challenges associated with incorporating a gum and more particularly a silicone gum, an antiperspirant composition may have a concentration of a silicone gum from about 0.1%, 0.3%, 0.4%, 0.5%, 0.6%, 0.7% or 0.8% to about 1.5%, 1.25%, 1%, 0.9%, 0.8%, 0.7%, 0.65, 0.5%, or 0.4% by weight of the antiperspirant composition. In some instances, the most preferred concentration of silicone gum by weight of the antiperspirant composition is from about 0.3% to about 0.8% in order to balance pattern diameter/quality with deposition. In some instances, the antiperspirant composition may have from about 0.1% to about 0.6% of a silicone gum when paired with a propellant concentration from 70% to 80% and a particulate concentration from 40% to 50%. In some instances, the antiperspirant composition may have from about 0.1% to about 0.4% of a silicone gum when paired with a propellant concentration from 70% to 80% and a particulate concentration from 50% to 60%. In some instances, the antiperspirant composition may have from about 0.3% to about 1.5% of a silicone gum when paired with a propellant concentration from 80% to 90% and a particulate concentration from 40% to 50%. In some instances, the antiperspirant composition may have from about 0.3% to about 1% of a silicone gum when paired with a propellant concentration from 80% to 90% and a particulate concentration from 50% to 60%. While it is believed to be very desirable to include a silicone gum in an antiperspirant composition comprising a non-volatile silicone fluid and at propellant concentrations from about 70% to about 90% or even about 95%, it is also contemplated that in some instances it may be desirable for the antiperspirant composition to be substantially or completely free of a silicone gum.

If a silicone gum is included, any silicone gum having a viscosity within the ranges described herein may be used, provided it is soluble in the liquid carrier, propellant or a combination thereof of the antiperspirant composition. Some suitable silicone gums include silicone polymers of the dimethyl polysiloxane type, which may have other groups attached, such as phenyl, vinyl, cyano, or acrylic, but the methyl groups should be in a major proportion. Silicone polymers having a viscosity below about 100,000 centistokes (molecular weight below about 100,000) at 25° C. are not considered silicone gums here but are rather, typically, considered a silicone fluid. One non-limiting example of silicone gum suitable for use is a silicone/gum fluid blend comprising a dimethiconol gum having a molecular weight form about 200,000 to 4,000,000 along with a silicone fluid carrier with a viscosity from about 0.65 to 100 mm$^2$ s$^{-1}$. An example of this silicone/gum blend is available from Dow Corning, Corp. of Michigan, USA under the trade name DC-1503 Fluid (88% dimethicone fluid/12% dimethiconol). Other silicone gums materials include SF1236 Dimethicone, SF1276 Dimethicone, and CF1251 Dimethicone available from Momentive Performance Materials, Inc. of NY, USA.

An antiperspirant composition is preferably substantially or completely free of water added as separate ingredient (i.e., anhydrous), as too much added water may result in several deleterious effects such as: 1) increasing the propensity for antiperspirant active particulates to agglomerate (thereby increasing the propensity for clogging), and 2) reducing dry feel on skin. It will be appreciated that even an anhydrous antiperspirant composition may still contain some water that is bound with an ingredient (e.g., antiperspirant active, tapioca material, etc.) otherwise added to the antiperspirant composition.

D. Particulate Materials

Delivering a sufficient concentration of particulates to the skin is believed to improve the skin feel of an antiperspirant composition comprising a high concentration of a non-volatile silicone fluid. It is believed that an antiperspirant composition comprising a total non-volatile liquid material to total particulate material ratio (L/P ratio) from about 0.6, 0.8, 1, 1.2, or 1.4 to about 1.6, 1.4, 1.2 or 1 may balance the tradeoff between enough particulates to provide acceptable skin feel while minimizing the appearance of residue. An antiperspirant composition may have a total particulate concentration from about 30%, 35%, or 40% to about 50% or 45% by weight of the antiperspirant composition.

The antiperspirant composition may comprise a variety of particulate materials. However, it is believed that the type (e.g., hydrophilic v. hydrophobic) and concentrations of particulate materials included in an antiperspirant composition may, in some instances, impact skin feel, release of the antiperspirant active, and the propensity for clogging in the spray device. For example, too much antiperspirant active may result in a wet or sticky skin feel due to the propensity of antiperspirant actives to become sticky when hydrated (e.g., by perspiration) even within the L/P ratios previously described. In addition, too much of a hydrophobic particulate material may reduce release of the antiperspirant active from the composition. Conversely, inclusion of a hydrophilic particulate material may advantageously aid release of the antiperspirant active, which may be beneficial in a composition comprising a high concentration of a non-volatile silicone fluid. However, hydrophilic materials may increase the risk of clogging in the presence of water. Therefore, it may be desirable to balance these and other design considerations when incorporating particulate materials in an antiperspirant composition comprising a non-volatile silicone fluid. It is believed that L/P ratios from about 1 to about 1.6 may be particularly beneficial in some instances for balancing the tradeoff between skin feel and residue in an antiperspirant composition comprising a non-volatile silicone fluid.

Some examples of particulate materials suitable for use include, but are not limited to, antiperspirant actives, powders (e.g., starch materials), encapsulated fragrance materials and bulking or suspending agents (e.g., silicas or clay materials). Other types of particulates may also be incorporated in an antiperspirant composition.

Antiperspirant Actives

An antiperspirant composition comprises one or more antiperspirant actives. The antiperspirant actives are in a particulate form (rather than being solubilized) in the antiperspirant composition. Therefore, it may be desirable that the antiperspirant composition is provided in a form other than an emulsion or is substantially or completely free of solubilizers for the antiperspirant active. The antiperspirant composition may be provided in the form of a liquid dispersion (including suspensions and colloids). This is in contrast to, for instance, WO 03/002082 which discloses solubilizing the antiperspirant active in an emulsion having a disperse phase and a continuous phase.

The compositions described herein may be free of, substantially free of, or may include an antiperspirant active (i.e. any substance, mixture, or other material having antiperspirant activity). The antiperspirant active may be any particle having antiperspirant activity. The antiperspirant active is preferably insoluble in the liquid components of the antiperspirant composition. Since the amount of antiperspirant active may significantly impact skin feel, an antiperspirant composition may comprise from about 14% 16%, 18%, 20%, 22%, or 24% to about 38%, 36%, 34%, 32%, 30%, 28%, or 26% by weight of a particulate antiperspirant active. In some instances, it may be desirable to utilize a low concentration of the antiperspirant active, such as less than 20% or 18% by weight of the antiperspirant composition. The antiperspirant active concentrations refer to the anhydrous amount that is added.

Some examples of suitable antiperspirant actives include astringent metallic salts, particularly including the inorganic and organic salts of aluminum. Some non-limiting examples exemplary aluminum salts that can be used include aluminum chloride and the aluminum hydroxyhalides having the general formula $Al_2(OH)_aQ_bXH_2O$ where Q is chloride, bromide, or iodide (preferably chloride), a is from about 2 to about 5, and a+b=about 6, and a and b do not need to be integers, and where X is from about I to about 6, and X does not need to be an integer. Particularly preferred are the aluminum chlorhydroxides referred to as "⅚ basic chlorhydroxide" wherein "a" is 5 and "⅔ basic chlorhydroxide" wherein "a" is 4. Aluminum salts of this type can be prepared in the manner described more fully in U.S. Pat. Nos. 3,887,692; 3,904,741; and 4,359,456. Preferred compounds include the ⅚ basic aluminum salts of the empirical formula $Al_2(OH)_5DI_2H_2O$; mixtures of $AlCl_3 6H_2O$ and $Al_2(OH)5Cl_2H_2O$ with aluminum chloride to aluminum hydroxychloride weight ratios of up to about 0.5. The antiperspirant active may be, for example, aluminum chlorohydrate.

The aluminum salt may be prepared by methods well known in the art. In some embodiments, the aluminum salts may be made by applying heat to a dilute aqueous solution of an aluminum salt (e.g., less than 20% of an aluminum salt by weight of the dilute solution) to form a solid aluminum salt comprising aluminum hydrolysis polymers. Some non-limiting examples of such methods are described in U.S. Pat. Nos. 4,871,525 and 4,359,456.

Substantially Inert Particulate Materials

The balance of the total particulate concentration of an antiperspirant composition may comprise excipient particulate materials that are substantially inert with respect to itself and/or antiperspirant active, meaning there are no significant particle to particle interactions with respect to itself and/or the antiperspirant active when present in the antiperspirant composition. Excipient particulate materials exclude clays and silicas added to an antiperspirant composition as bulking or suspending agents, as these particles can exhibit strong particle to particle interactions. The excipient particulate materials may be either hydrophilic or hydrophobic (including hydrophobically modified, which tend to be moderately hydrophobic). Some non-limiting examples of substantially inert excipient particulate materials that may be included in an antiperspirant composition include, but are not limited to, encapsulated fragrance materials; native starches such as tapioca, corn, oat, potato, and wheat starch particulates or hydrophibically modified versions of these starches; talc; calcium carbonate; perlite; mica and polyethylene beads. One non-limiting example of a hydrohobically modified corn starch material suitable for use comprises aluminum starch octenylsuccinate, which is available under the trade name Dry Flo PC or Dry Flo Pure from Akzo Nobel, Netherlands. The substantially inert particulates may be free flowing. An antiperspirant composition may comprise from about 0.25%, 0.5%, 1%, 5%, 10%, 12%, or 14% to about 25%, 22%, 20%, 18%, or 16% by weight of the antiperspirant composition of substantially inert particulates. One substantially inert particulate material believed to be suitable for use is a hydrophilic or hydrophobically modified tapioca starch material. A tapioca starch material may be particularly beneficial as it is unlikely to induce an allergic reaction if inhaled. Tapioca is a starch which may be extracted from the cassava plant, typically from the root, which may then be processed or modified as known in the art. Tapioca starches are, advantageously, substantially non-allergenic. One non-limiting example of a hydrophobically modified tapioca starch material suitable for use comprises a silicone grafted tapioca starch, which is available under the trade name Dry Flo TS from AkzoNobel of the Netherlands. The INCI name is tapioca starch polymethylsilsesquioxane and may be produced by a reaction of methyl sodium siliconate (polymethylsilsesquioxane) and tapioca starch. This silicone grafted tapioca starch material is commercially available as CAS No. 68989-12-8. The silicone grafted tapioca starch material can be formed using any known means, including, but not limited to those methods described in U.S. Pat. Nos. 7,375,214, 7,799,909, 6,037,466, 2,852,404, 5,672,699, and 5,776,476. Other non-limiting examples of hydrophobically modified tapioca starch materials that are suitable for use include Dry Flo AF (silicone modified starch from Akzo Nobel), Rheoplus PC 541 (Siam Modified Starch), Acistar RT starch (available from Cargill) and Lorenz 325, Lorenz 326, and Lorenz 810 (available from Lorenz of Brazil). In some specific embodiments, the tapioca starch material may be hydrophilic in order to facilitate release of the antiperspirant active during use. One non-limiting example of a hydrophilic tapioca starch material suitable for use is available under the trade name Tapioca Pure available from Akzo Nobel. In some specific embodiments, the substantially inert particulate material comprises a hydrophilic tapioca material, a hydrophobic tapioca material or a mixture thereof.

An antiperspirant composition may optionally comprise one or more particulate fragrance carriers or materials that may or may not encapsulate a perfume component. Fragrance carriers are typically particulates, which would be considered part of the total particulate concentration of an antiperspirant composition. The fragrance carriers are preferably hydrophobic in order to minimize particle-to-particle interactions. The fragrance carriers may be either full or empty. A full fragrance carrier is a fragrance carrier that encapsulates or otherwise contains a perfume component while the fragrance carrier is stored within the spray device. Full fragrance carriers may release their perfume components by a variety of mechanisms post delivery from the spray device to provide a desired aroma or fragrance experience for a user. For example, the perfume components may be released by moisture upon wetting of the fragrance carrier, e.g., by perspiration or other body fluids. Alternatively or in addition thereto, the perfume components may be released by fracture of the carrier, such as by the application of pressure or a shearing force. An empty fragrance carrier is a fragrance carrier that does not contain a perfume component while stored within the spray device. One non-limiting example of an empty fragrance carrier is an uncomplexed cyclodextrin material.

Some non-limiting examples of fragrance carriers suitable for encapsulating a perfume component include, but are not limited to, oligosaccharides (e.g., cyclodextrins), starches, polyethylenes, polayamides, polystyrenes, polyisoprenes, polycarbonates, polyesters, polyacrylates, vinyl polymers, silicas, and aluminosilicates. Some examples of fragrance carriers are described in USPNs 2010/0104611; 2010/0104613; 2010/0104612; 2011/0269658; 2011/0269657; 2011/0268802; U.S. Pat. Nos. 5,861,144; 5,711,941; 8,147,808; and 5,861,144.

An antiperspirant composition may comprise from about 0.25%, 0.5%, 0.75%, 1%, or 2% to about 20%, 16%, 12%, 10%, 8%, 6% or 4% by weight of the antiperspirant composition of fragrance carriers. In some instances, the substantially inert excipient particles of the antiperspirant composition consist essentially of or completely of full fragrance carriers, empty fragrance carriers, or mixtures thereof. An antiperspirant composition may comprise from about 0.25%, 0.5%, 0.75%, or 1% to about 6%, 4% or 2% by weight of the antiperspirant composition of full fragrance carriers. An antiperspirant composition may comprise from about 0.25%, 0.5%, 1%, or 2% to about 16%, 12%, 10%, 8%, 6% or 4% by weight of the antiperspirant composition of empty fragrance carriers. In some instances, it may be desirable to incorporate a mixture of empty fragrance carriers and full fragrance carriers in the antiperspirant composition, wherein the empty fragrance carriers may be included to achieve the desired overall particulate concentration without the risk of perfume over-dosing.

In some instances, it may be desirable to provide a mixture of fragrance carriers and native starch powders to achieve the desired particle concentration. For example, from about a 20:80 to 80:20 (fragrance carrier to starch) mixture might be utilized. In some instances, a 50:50 mixture might be utilized and in other instances the native starch powders might have a concentration equal to about or less than 6% by weight of the antiperspirant composition while the concentration of the fragrance carriers might be equal to about or less than 9% by weight of the antiperspirant composition.

A wide variety of perfume components may be used with the fragrance carriers, including but not limited to volatile perfume components having a boiling point at normal pressure of less than about 260° C., more preferably less than about 250° C., and perfume components having significant low odor detection threshold, and mixtures thereof. The boiling points of many perfume components are given in, e.g., "Perfume and Flavor Chemicals (Aroma Chemicals)," Steffen Arctander, published by the author, 1969.

Bulking and Suspending Agents

An antiperspirant composition may comprise a bulking or suspending agent. In some instances, it may be desirable to include a bulking or suspending agent in the antiperspirant composition in order to reduce the risk of caking of the antiperspirant composition at the bottom of the container and/or to aid in the redispersion of the antiperspirant composition upon shaking without significant clumping so as to reduce the risk of clogging any small orifices within the spray device. This may be particularly useful as antiperspirant actives are dense and tend to settle quickly and/or may be prone to caking in the presence of moisture. Significant settling and/or agglomeration of particulates in an antiperspirant composition may complicate delivery of a uniform dose of the antiperspirant active from a spray device. This in turn may negatively impact skin feel or contribute to the appearance of a white residue. While other solutions for addressing redispersion, settling and/or caking may be employed, there may also be tradeoffs involved. For example, U.S. Pat. No. 7,815,899 suggests utilizing a high viscosity polymeric material (e.g., a quarternary ammonium functional silicone) to reduce the settling rate. However, this approach may, in some instances, have tradeoffs. For example, some quaternary silicones have a strong odor from amine impurities that can interfere with fragrance of the product. Moreover, these amines may negatively interact with the active via a lewis acid/base reaction.

The bulking or suspending agent may be hydrophobic, hydrophilic or comprise mixtures thereof. In some specific embodiments, these materials may be hydrophilic in order to facilitate release of the antiperspirant active during use. Some examples of silica materials that may be used include, but are not limited to, colloidal silicas. Some non-limiting examples of silica materials are available from Evonik Industries under the trade names Aerosil 200SP, Aerosil 300SP and Aerosil R972.

In some instances, the antiperspirant composition may include a clay material. Some non-limiting examples of clay materials include montmorillonite clays and hydrophobically treated montmorillonite clays. Montmorillonite clays are those which contain the mineral montmorillonite and may be characterized by a having a suspending lattice. Some examples of these clays include but are not limited to bentonites, hectorites, and colloidal magnesium aluminum silicates. Some non-limiting examples of organoclays include modified bentonite, modified hectorite, modified montorlinite and combinations thereof, some examples of which are available under the trade names Bentone 27 (stearalkonium bentonite), Bentone 34 (stearalkonium bentonite) and Bentone 38 (disteardimonium hectorite) from Elementis Specialities Plc. and Tixogel VPV (quaternium 90-bentonite), Tixogel VZV (stearalkonium bentonite), Tixogel LGM (stearalkonium bentonite) and Claytone SO (stearalkonium bentonite) from Southern Clay Products.

The antiperspirant composition may also comprise a clay activator, such as propylene carbonate, triethyl citrate, methanol, ethanol, acetone, water and mixtures and derivatives thereof. Clay activators may also strongly interact with an antiperspirant active (e.g., leading to clumping or coating of the antiperspirant active and/or changes in active polymer structure which may reduce antiperspirant efficacy). Therefore, it may be desirable to limit the amount of clay activator present in the antiperspirant composition to between about 0.5%, 0.75%, 1%, 1.25%, or 1.5% to about 3%, 2%, or 1.75% by weight of the antiperspirant composition.

III. Spray Devices

In order to avoid over-dosing of the antiperspirant composition, it is desirable that the spray device have a total mass flow rate of the propellant/antiperspirant composition mixture of less than 1.25 grams/sec or from about 0.5 grams/sec to about 1.3 grams/sec, or from about 0.6 grams/sec to about 1.0 grams/sec, or from about 0.7 grams/sec to about 1.0 grams/sec. The spray device may have an antiperspirant composition mass flow rate less than 0.3 grams/sec or from about 0.1 grams/sec to about 0.3 grams/sec or from about 0.1 grams/sec to 0.2 grams/sec or from about 0.15 grams/sec to about 0.2 grams/sec. It is believed that mass flow rates greater than described above may lead to a wet or sticky skin feel because the total amount of antiperspirant composition deposited on the skin may be too great.

The amount of antiperspirant active delivered to a target surface by a two second application from a spray device may be from about 40 mg, 50 mg, 60 mg, or 70 mg to about 100 mg, 90 mg, or 80 mg. The total amount of antiperspirant composition delivered to a target surface by a two second application of a spray device may be from about 0.1 grams to about 0.4 grams, or from about 0.2 grams to about 0.4 grams, or from about 0.2 grams to about 0.3 grams. The amount of liquid fragrance material delivered to a target surface by a two second application of a spray device may be from about 3 mg to about 20 mg, or from about 6 mg to about 15 mg, or from about 6 mg to about 12 mg. The amount of full fragrance carriers delivered to a target surface by a two second application of a spray device may be from about 0.75 mg to about 15 mg, or from about 1 mg to about 12 mg, or from about 1 mg to about 9 mg. The spray device may have a deposition efficiency, of either the antiperspirant composition and/or the antiperspirant active and/or the liquid fragrance material, that is from about 50%, 55%, 60%, 70% or 75% to about 85%, 80%, or 75%.

One example of a non-limiting valve assembly suitable for use is described in U.S. Pat. No. 4,396,152. One example of a valve assembly is available from the Precision Valve Company (USA) under the trade name Ecosol.

A user of a spray device may initiate a spray by depressing an actuator, thereby opening a valve which enables a liquid propellant/antiperspirant composition mixture to exit the actuator. Prior to actuation, it may be desirable to shake or rotate the product to redisperse the liquid and particulate materials. While usage time can vary widely, users may depress the actuator from about 2 seconds to about 5 seconds, or from about 2 seconds to about 4 seconds, or from about 2 seconds to about 3 seconds to provide a burst of antiperspirant composition for deposition to an underarm or axillia skin surface. A spray device may be sized to provide a total spray time from about 60 seconds to about 200 seconds, or from about 70 seconds to about 150 seconds, for from about 90 seconds to about 130 seconds, thereby providing from about 15 to about 50 two second uses before exhaustion.

Table 3 shows Samples that are also antiperspirant composition formulations that may be used to make an aerosol antiperspirant product with the inventive processes described herein:

TABLE 3

| Ingredient | Sample 6 | Sample 7 | Sample 8 | Sample 9 | Sample 10 | Sample 11 | Sample 12 | Sample 13 |
|---|---|---|---|---|---|---|---|---|
| Aluminum chlorohydrate[1] | 26% | 40% | 26% | 40% | 48% | 26% | 40% | 50% |
| Dimethicone - 50 centistoke | 48.04% | 48.04% | 32.04% | 32.04% | 32.04% | 35.04% | 35.04% | 35.04% |
| Hydrophilic tapioca[2] | 12% | 0% | 19% | 5% | 0% | 26% | 12% | 2% |
| Disodium Hectorite[3] | 3% | 3% | 3% | 3% | 3% | 3% | 3% | 3% |
| Triethyl citrate | 0.96% | 0.96% | 0.96% | 0.96% | 0.96% | 0.96% | 0.96% | 0.96% |
| Betacyclodextrin fragrance | 3% | 1% | 3% | 3% | 3% | 3% | 3% | 3% |
| Silicone gum[4] | 0.5% | 0.5% | 0.5% | 0.5% | 0.5% | 0.5% | 0.5% | 0.5% |

The values are shown on a by weight of the antiperspirant composition basis.
[1]86% assay of anhydrous active, average particle size approximately 15 microns.
[2]Tapioca Pure available from Akzo Nobel
[3]Bentone 38 available from Elementis
[4]DC1503 (a mixture of dimethicone and dimethiconol) available from Dow Corning. DC1503 comprises approximately 12% by weight of the mixture of a silicone gum (dimethiconol).

EXAMPLES

The following Table 2 shows Samples 1, 3, and 4 that are antiperspirant composition formulations, by weight % of the antiperspirant composition, that may be used to make an aerosol antiperspirant product with the inventive processes described herein. Also shown are Samples 2 and 5, which include cyclopentasiloxane.

TABLE 2

| Ingredients | Sample 1 | Sample 2 | Sample 3 | Sample 4 | Sample 5 |
|---|---|---|---|---|---|
| Dimethicone, 5 cst | 38.35 | | 34.25 | 38.35 | |
| Aluminum Chlorohydrate (86% Active)(drum) | 28.72 | 28.72 | 28.72 | 28.72 | 28.72 |
| Aluminum Starch Octenylsuccinate | 10.23 | 10.23 | 10.23 | 10.23 | 10.23 |
| Datura BCD Complex with Pharma grade BCD | 10.23 | 10.23 | 10.23 | 10.23 | 10.23 |
| C12-15 ALKYL BENZOATE | 4.10 | 4.10 | 8.20 | 4.10 | 4.10 |
| Dimethicone 50 cst | 4.10 | 4.10 | 4.10 | 4.10 | 4.10 |
| Disteardimonium Hectorite | 2.05 | 2.05 | 2.05 | 2.05 | 2.05 |
| Mineral Oil Light White 10046903 | 1.03 | 1.03 | 1.03 | 1.03 | 1.03 |
| Triethyl citrate | 0.68 | 0.68 | 0.68 | | |
| Dimethicone (and) Dimethiconol | 0.51 | 0.51 | 0.51 | 0.51 | 0.51 |
| Cyclopentasiloxane (D5) | | 38.35 | | | 38.35 |
| Propylene Carbonate | | | | 0.68 | 0.68 |

Figure 4:
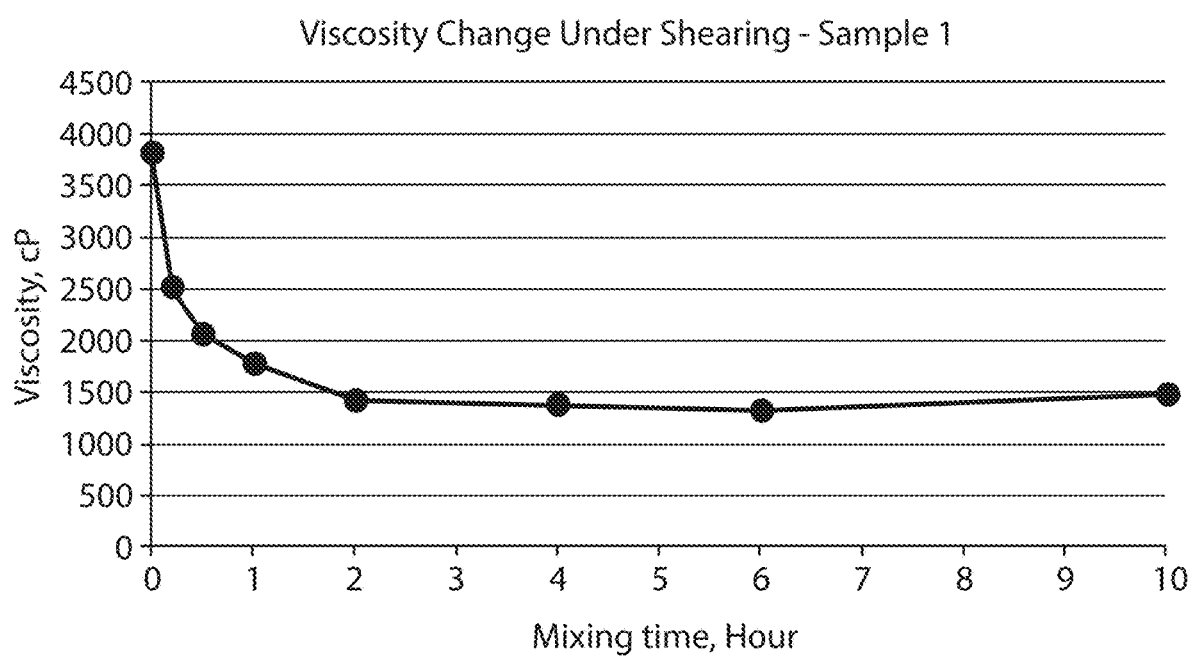
FIG. 4 is a graph showing viscosity change under shearing.
Figures 5, 6:
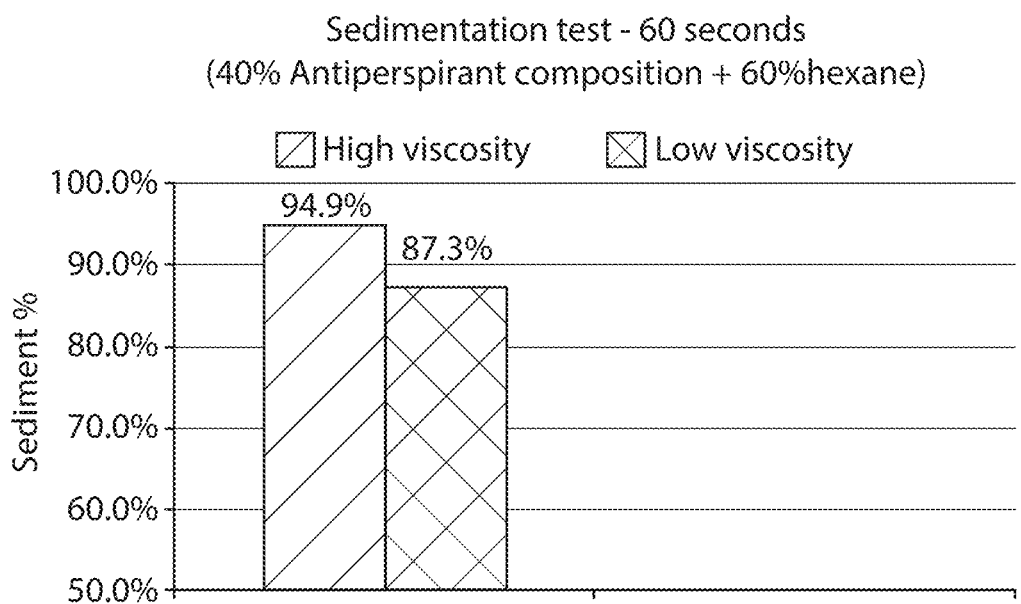
FIG. 5 is a table showing the data from FIG. 4.
FIGS. 6 and 7 are graphs of sedimentation tests of an antiperspirant composition in hexane.

FIGS. 4 and 5 show the decrease in viscosity as a function of time for an aerosol composition such as Sample 1, after the components of the aerosol composition were combined in a 17,000 liter tank with agitation at 50 rpm. The viscosity of the aerosol composition drops from 3825 cP to 1,420 cP after 2 hours and is 1,480 cP after 10 hours. If this aerosol composition were taken from the tank and filled into spray devices without a milling step before the filling, the low viscosity of less than 2,000 cP can cause the aerosol product to compact. This compaction may require that the aerosol product (the aerosol composition plus propellant) requires more vigorous shaking than what a typical consumer may provide, thus increasing incidences of the spray device nozzle clogging and/or choking.

Table 4 shows that viscosity builds when an aerosol composition is milled. Table 4 shows the viscosities for aerosol composition Samples 1-5 when nothing has been done to them but mixed (sheared) for 90 minutes. The Samples were then milled, and Table 4 then shows the resulting higher viscosities. These higher viscosities after a milling step would be roughly the viscosities at the time of filling in the present invention, as the filling is done at most 2 hours after the milling that builds the viscosity. As can be seen, Samples 2 and 5, which have cyclopentasiloxane, both begin with and rise to higher viscosities. Samples 1, 3, and 4, which do not have cyclopentasiloxane, have lower beginning viscosities, thus benefitting from the re-milling step immediately before filling that raises their viscosities.

TABLE 4

| | Sample 2 | Sample 5 | Sample 3 | Sample 1 | Sample 4 |
|---|---|---|---|---|---|
| Sheared for 90 minutes | 4800 | 2450 | 2440 | 1900 | 1320 |
| Re-milling before filling | 12125 | 10250 | 5380 | 3750 | 2200 |

Figure 7:
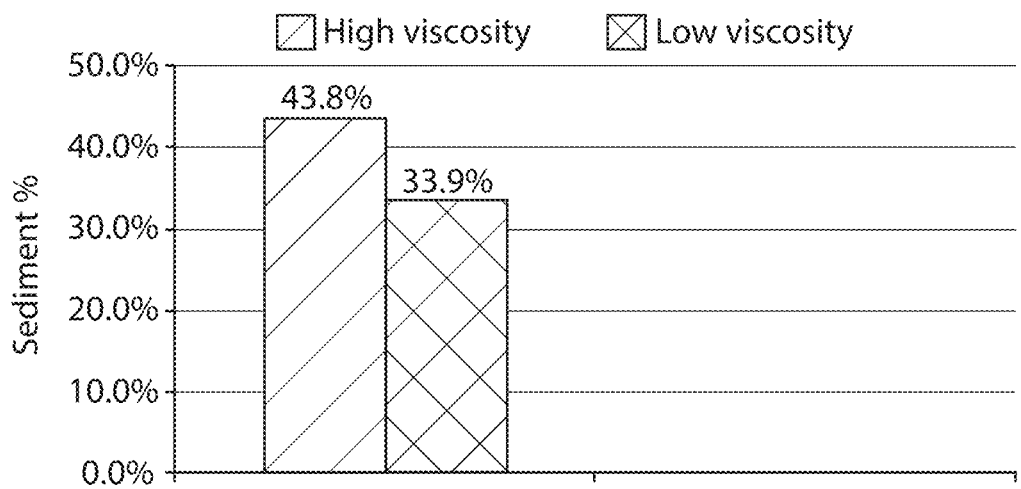

FIGS. 6 and 7 show the sediment % for aerosol products (antiperspirant composition plus surrogate propellant) containing high and low viscosity antiperspirant compositions. Sample 1 from Table 2 was made two different ways. In the first way, the time between the final milling and the filling of the spray device with the antiperspirant composition was at least 6 hours. This is referred to as the low viscosity product in FIGS. 6 and 7. The second way involved a milling of the antiperspirant composition within 2 hours, specifically about 10 to 20 minutes, before being filled into a spray device, which is referred to as the high viscosity product in FIGS. 6 and 7. Both antiperspirant compositions were then used to make corresponding antiperspirant products comprising 40% Sample 1 and 60% hexane as a surrogate propellant. Hexane, while not itself being a propellant, results in similar behavior of the antiperspirant composition, while allowing the antiperspirant composition to be observed and measured according to the Sedimentation Test described below. In FIGS. 6 and 7, the two products underwent the Sedimentation Test, once at 60 seconds (FIG. 6) and again at 24 hours (FIG. 7).

FIG. 6 is the sediment % at 60 seconds after shaking the spray devices. As can be seen, the aerosol product with the high viscosity antiperspirant composition has a greater sediment %. This indicates less compaction of the antiperspirant composition. A higher sediment % indicates a slower separating or settling of the antiperspirant composition, so that the aerosol product is more quickly and easily returned to a completely homogeneous product with shaking. Ultimately, the higher sediment % for the high viscosity antiperspirant composition indicates that the resulting aerosol product, due to the time between milling and filling being at most 2 hours, will be less likely to clog or choke the nozzle of a spray device. Similarly, FIG. 7 shows the sediment % at 24 hours after shaking the spray devices containing the two aerosol products, low viscosity and high viscosity. Again, the high viscosity product had a higher sediment %.

Figure 8:
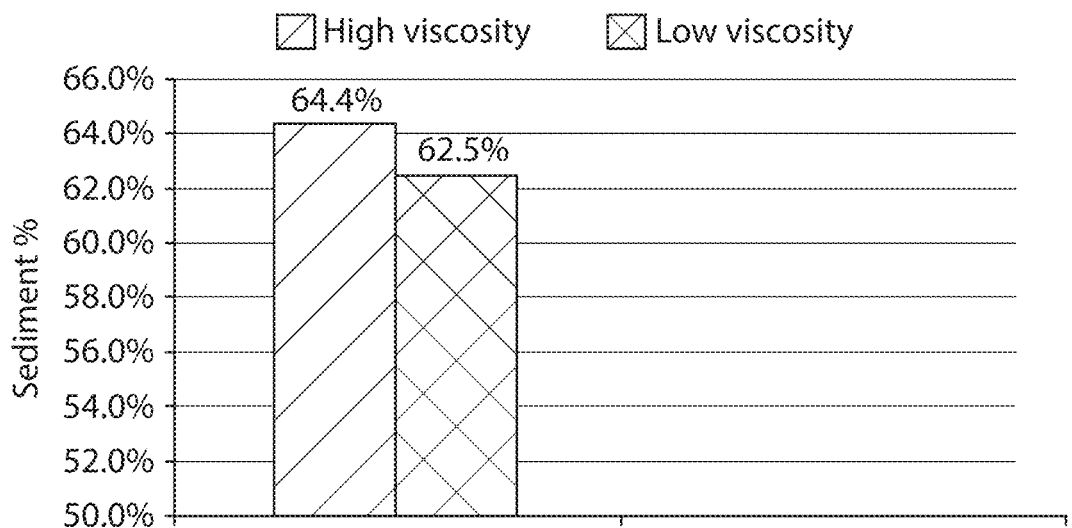
FIG. 8 is a graph of a centrifuge compaction test of an antiperspirant composition in hexane.

FIG. 8 shows the sediment % via a centrifuge compaction test for two products made comprising 87.5% Sample 1 antiperspirant composition and 12.5% hexane as a surrogate propellant. Again, one was made with at least 6 hours between the final milling and the filling of the antiperspirant composition into a spray device (low viscosity), and the other was made with a milling within 2 hours of being filled into a spray device (high viscosity). Again, the high viscosity antiperspirant composition results in a higher sediment %.

Figure 9:
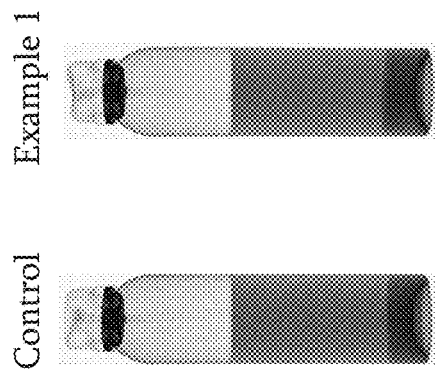
FIG. 9 shows x-ray photos of two aerosol products.

FIG. 9 shows x-rays of two aerosol products, in which the only difference between the products was the time between the final milling of the antiperspirant composition and the filling of the antiperspirant composition into a spray device. Both aerosol products comprise Sample 1 in Table 2 above as the antiperspirant composition. The control aerosol product's antiperspirant composition was filled into its spray device at least 6 hours after being milled. The inventive Example 1 aerosol product's antiperspirant composition was filled into its spray device about 15 minutes after being milled, with a process as depicted in FIG. 2. Both antiperspirant compositions were combined at a ratio, by weight, of 40% antiperspirant composition and 60% propellant, where the propellant for both was 66% A-17 and 34% 152A. Both products rested for 56 days.

Figure 10:
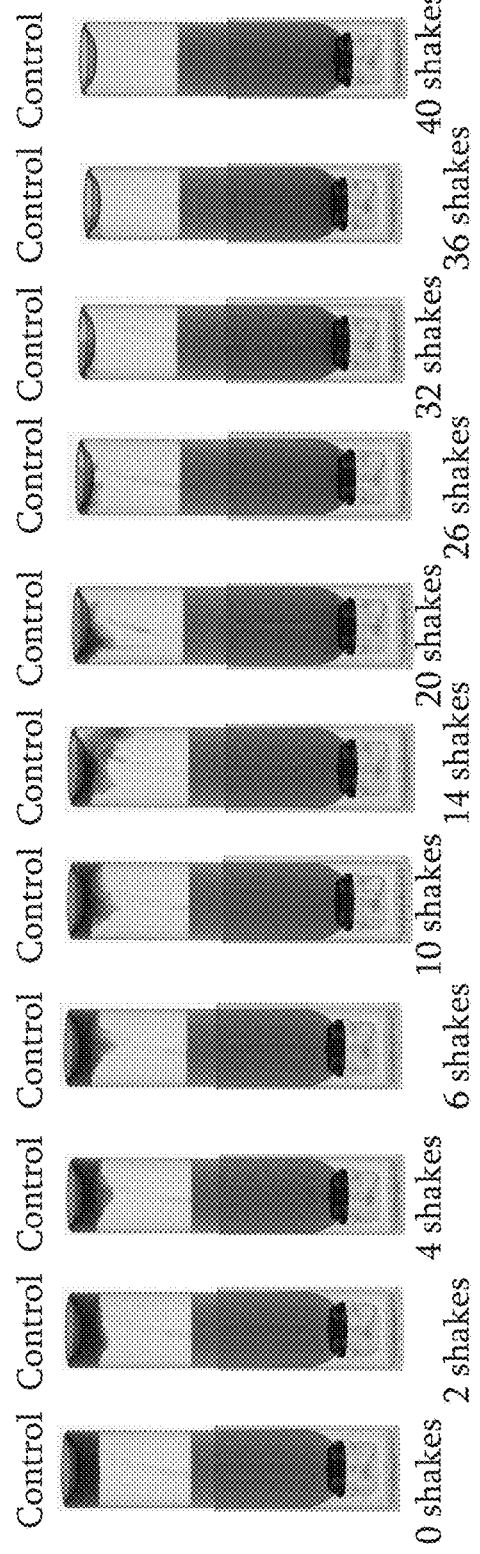
FIG. 10 shows x-ray photos of an aerosol product during a Shaking Can Test.
Figure 11:
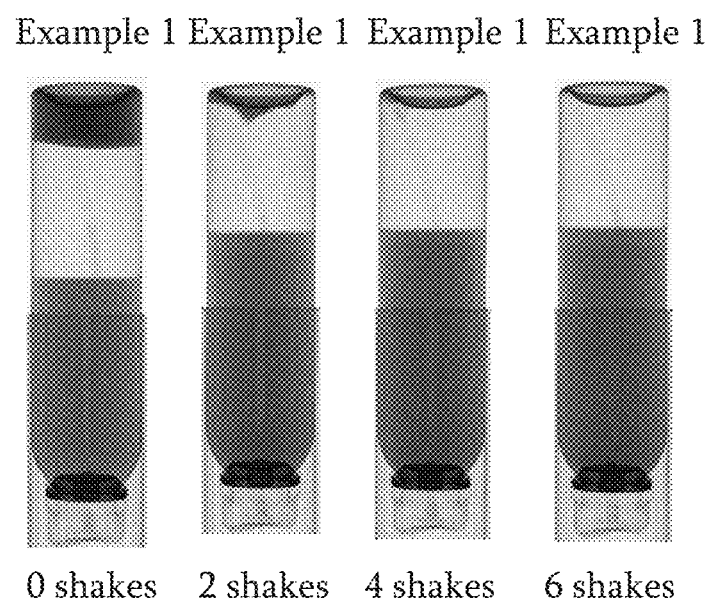
FIG. 11 shows x-ray photos of an aerosol product during a Shaking Can Test.

As can be seen in the x-rays shown in FIG. 9, the height of sediment in Example 1 was higher than the height of sediment in the control. The sediment height was 11.9 mm for the control and 14.5 mm for Example 1. The greater sediment height for Example 1 indicates the unexpected importance of a milling step immediately before removing a portion to be filled into a spray device, by showing that less compaction occurred. Similarly, FIG. 10 shows x-rays of the control and FIG. 11 of Example 1 as they are shaken via the Shaken Can Test Method described below. The control in FIG. 10 required roughly 40 shakes to redisperse the sediment and compaction into a homogeneous product, while for Example 1 shown in FIG. 11, after 6 shakes, the sediment is fully dispersed.

Test Methods

Sedimentation Test—60 Seconds, 24 Hours

Use an 8 oz glass jar with lid, add 40 grams of antiperspirant composition and 60 grams of hexane, and shake sample well to ensure complete mixing/dispersion. Allow the jars to sit undisturbed for 60 seconds or 24 hours, measure the height of sediment and the total height of the content inside the jar. Calculate sediment percentage as height of the sediment/height of total content.

Centrifuge Compaction Test

Use a 40 ml centrifuge tube with lid and Thermo Scientific Heraeus Labofuge 400. Add 5 grams of hexane and 35 grams of antiperspirant composition, shake sample well to ensure complete mixing/dispersion. Then place the samples in the centrifuge tube holders and spin for 30 minutes at 2500 rpm. Measure the height of sediment and the total height of the content inside the jar. Calculate sediment percentage as height of the sediment/height of total content.

Shaking Can Test

Purpose: Quantify the number of shakes that is needed for the cake on bottom of a product can to be completely dislodged/re-dispersed by a typical consumer.

Procedure:

Invert the can (bottom-up) and take an x-ray image of the can and inspect the cake to make sure the cake has not been disturbed or shaken during sample handling or transportation; hold the can upright and shake the can up and down; invert the can and take an x-ray image of the cake/can; inspect the cake or any lumps in the liquid layer; repeat till the cake is completely dislodged and dispersed. Duplicate samples are recommended.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All numeric values (e.g., dimensions, flow rates, pressures, concentrations, etc.) recited herein are modified by the term "about", even if not expressly so stated with the numeric value.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making an aerosol antiperspirant product, the method comprising:
   combining components to form an antiperspirant composition, said components selected from the group consisting of an antiperspirant active, a carrier, a suspending agent, day activator, and combinations thereof;
   milling the composition;
   re-milling the composition;
   depositing the composition into a spray device at most 2 hours after re-milling of the composition, wherein the viscosity of the composition while being deposited is at least about 2000 cP; and
   adding a propellant to the composition in the spray device; wherein the composition does not include cyclopentasiloxane.

2. The method of claim 1, wherein the method further comprises the step of adding at least one perfume or fragrance.

3. The method of claim 2, wherein the step of adding a perfume or fragrance is after the milling of the composition and before depositing the composition into a spray device.

4. The method of claim 1, wherein the composition further comprises silicone gums or skin feel modifiers.

5. The method of claim 1, wherein the antiperspirant composition is anhydrous.

6. The method of claim 1, further comprising a step of filtering the composition after milling the composition and before adding a propellant.

7. The method of claim 1, wherein the composition is deposited into a spray device at most about 1 hour after re-milling the composition.

8. The method of claim 1, wherein the composition comprises a carrier that is a nonvolatile linear silicone fluid with nine or more average silicone atoms.

9. The method of claim 1, wherein the viscosity of the antiperspirant composition is at least about 4000 cP.

10. The method of claim 1, wherein the components of the antiperspirant composition are at least about 500 kilograms.

11. A method of making an aerosol antiperspirant product, the method comprising;
    combining components to form an antiperspirant composition, said components selected from the group consisting of an antiperspirant active, a carrier, a suspending agent, a clay activator, and combinations thereof, and said antiperspirant composition not comprising cyclopentasiloxane;
    milling the composition;
    re-milling the composition;
    depositing the composition into a spray device at most 2 hours atter re-milling of the composition;
    wherein the viscosity of the composition deposited into the spray device is at least about 2000 cP.

12. The method of claim 11, further comprising the step of adding a propellant to the composition in the spray device.

13. The method of claim 11, further comprising the step of adding a perfume to the composition.

14. The method of claim 11, wherein the viscosity of the antiperspirant composition is at least about 4000 cP.

* * * * *